United States Patent [19]
Gill et al.

[11] Patent Number: 5,258,180
[45] Date of Patent: Nov. 2, 1993

[54] TISSUE PLASMINOGEN ACTIVATOR HAVING FIBRIN SPECIFIC PROPERTIES AND DELETION OF AMINO ACIDS 466-970, COMPOSITIONS AND METHODS OF TREATMENT

[75] Inventors: John F. Gill, Redwood City; Leonard G. Presta; Mark J. Zoller, both of San Francisco, all of Calif.

[73] Assignee: Genetech, Inc., South San Francisco, Calif.

[21] Appl. No.: 744,614

[22] Filed: Aug. 13, 1991

Related U.S. Application Data

[60] Division of Ser. No. 486,657, Mar. 1, 1990, Pat. No. 5,156,969, which is a continuation-in-part of Ser. No. 384,608, Jul. 24, 1989, Pat. No. 5,108,901, which is a continuation-in-part of Ser. No. 240,856, Sep. 2, 1988, abandoned.

[51] Int. Cl.⁵ .................. C12N 9/64; C12N 15/58
[52] U.S. Cl. .................. 424/94.64; 424/94.63; 435/212; 435/219; 435/226
[58] Field of Search .................. 435/212, 219, 226; 424/94.63, 94.64

[56] References Cited

FOREIGN PATENT DOCUMENTS

| | | |
|---|---|---|
| 0199574 | 10/1986 | European Pat. Off. . |
| 0201153 | 11/1986 | European Pat. Off. . |
| 0225286 | 6/1987 | European Pat. Off. . |
| 0227462 | 7/1987 | European Pat. Off. . |
| 0233013 | 8/1987 | European Pat. Off. . |
| 0290118 | 11/1988 | European Pat. Off. . |
| 0292009 | 11/1988 | European Pat. Off. . |
| 0293934 | 12/1988 | European Pat. Off. . |
| 0293936 | 12/1988 | European Pat. Off. . |
| 0297066 | 12/1988 | European Pat. Off. . |
| 0299706 | 1/1989 | European Pat. Off. . |
| 0241209 | 10/1989 | European Pat. Off. . |
| WO8401960 | 11/1983 | PCT Int'l Appl. . |
| WO8601538 | 8/1985 | PCT Int'l Appl. . |
| WO8704722 | 8/1987 | PCT Int'l Appl. . |
| WO8805081 | 7/1988 | PCT Int'l Appl. . |
| WO8810119 | 12/1988 | PCT Int'l Appl. . |
| WO8900191 | 1/1989 | PCT Int'l Appl. . |

OTHER PUBLICATIONS

Tate et al., Biochemistry 26:338-343 (1987).
Peterson et al., Biochimica et Biophysica Acta 952:245-254 (1988).
Rijken et al., J. of Biol. Chem. 257:2920-2925 (1982).
Ross et al., Annual Reports in Medicinal Chemistry 23:111-120 (1988), Academic Press, Richard C. Allen, Ed.
Pannekoek et al., Fibrinolysis 2:123-132 (1988).
Huber et al., Accounts of Chemical Research 11:114-122 (1978).
Madison et al., Nature, 339:721-724 (1989).
D. Ringe, Nature, 339:658-659 (1989).

Primary Examiner—Robert J. Hill, Jr.
Assistant Examiner—Marianne Porta Allen
Attorney, Agent, or Firm—Ginger R. Dreger

[57] ABSTRACT

A tissue plasminogen activator (t-PA) variant is prepared that has an amino acid deletion at positions 466 to 470 of the corresponding wild-type t-PA. This alteration renders the variant fibrin (and plasma clot) specific as compared to the corresponding wild-type t-PA. DNA sequences can be prepared that encode the variant, as well as expression vectors incorporating the DNA sequences, and host cells transformed with the expression vectors. The variant may be used in a pharmaceutical preparation to treat a vascular disease or condition or to prevent fibrin deposition or adhesion formation or reformation in mammals.

10 Claims, 1 Drawing Sheet

Fig. 1.

TISSUE PLASMINOGEN ACTIVATOR HAVING FIBRIN SPECIFIC PROPERTIES AND DELETION OF AMINO ACIDS 466-970, COMPOSITIONS AND METHODS OF TREATMENT

This is a divisional of co-pending application Ser. No. 07/486,657 filed on 1 Mar. 1990 now U.S. Pat. No. 5,156,969, which is a continuation-in-part application of copending U.S. Ser. No. 07/384,608 filed Jul. 24, 1989, now U.S. Pat. No. 5,108,901 which is a continuation-in-part application of U.S. Ser. No. 07/240,856 filed Sep. 2, 1988 now abandoned.

BACKGROUND OF THE INVENTION

Field of the Invention

The present invention is directed to particular tissue plasminogen activator (t-PA) variants having a modified structure that includes deleted amino acids within the protease domain of t-PA, which modification renders the variant more fibrin (or plasma clot) specific than wild-type (wt) t-PA.

Description of Background and Related Art

Plasminogen activators are enzymes that activate the zymogen plasminogen to generate the serine proteinase plasmin (by cleavage at Arg561-Val562) that degrades various proteins, including fibrin. Among the plasminogen activators studied are streptokinase, a bacterial protein, urokinase, an enzyme synthesized in the kidney and elsewhere and originally extracted from urine, and human tissue plasminogen activator (t-PA), an enzyme produced by the cells lining blood vessel walls.

The mechanism of action of each of these plasminogen activators differs: Streptokinase forms a complex with plasminogen or plasmin, generating plasminogen-activating activity, urokinase cleaves plasminogen directly, and t-PA, fibrin, and plasminogen all interact to yield maximum activity.

t-PA has been identified and described as a particularly important and potent new biological pharmaceutical agent that has shown extraordinary results in the treatment of vascular diseases, such as myocardial infarction, due in part to its high fibrin specificity and potent ability to dissolve blood clots in vivo.

Although the existence of t-PA prompted numerous investigations by several scientific groups, it was first identified as a substantially pure isolate from a natural source, and tested for requisite plasminogen activator activity in vivo, by Collen et al., U.S. Pat. No. 4,752,603 issued Jun. 21, 1988. See also Rijken et al., *J. Biol. Chem.*, 256: 7035 (1981).

Subsequently, t-PA was fully identified and characterized by underlying DNA sequence and deduced amino acid sequence based on successful work employing recombinant DNA technology resulting in large quantities of t-PA in a distinct milieu. This work was reported by Pennica et al., *Nature*, 301: 214 (1983)) and in U.S. Pat. No. 4,766,075, issued 23 Aug. 1988.

Based on these disclosures, it seems now clear that the t-PA molecule contains five domains that have been defined with reference to homologous or otherwise similar structures identified in various other proteins such as trypsin, chymotrypsin, plasminogen, prothrombin, fibronectin, and epidermal growth factor (EGF). These domains have been designated, starting at the N-terminus of the amino acid sequence of t-PA, as 1) the finger region (F) that has variously been defined as including amino acids 1 to about 44, 2) the growth factor region (G) that has been variously defined as stretching from about amino acids 45 to 91 (based upon its homology with EGF), 3) kringle one (K1) that has been defined as stretching from about amino acid 92 to about amino acid 173, 4) kringle two (K2) that has been defined as stretching from about amino acid 180 to about amino acid 261, and 5) the so-called serine protease domain (P) that generally has been defined as stretching from about amino acid 264 to the C-terminal end of the molecule. These domains, which are situated generally adjacent to one another, or are separated by short "linker" regions, account for the entire amino acid sequence of from 1 to 527 amino acids of the putative mature form of t-PA.

Each domain has been described variously as contributing certain specific biologically significant properties. The finger domain has been characterized as containing a sequence of at least major importance for high binding affinity to fibrin. (This activity is thought important for the high specificity that t-PA displays with respect to clot lysis at the locus of a fibrin-rich thrombus.) The growth factor-like region likewise has been associated with cell surface binding activity. The kringle 2 region also has been strongly associated with fibrin binding and with the ability of fibrin to stimulate the activity of t-PA. The serine protease domain is responsible for the enzymatic cleavage of plasminogen to produce plasmin.

Despite the profound advantages associated with natural double-chain t-PA as a clot-dissolving agent and the advantage of natural single-chain pro-t-PA reported in EP Publ. No. 112,122, it is not believed that the natural protein necessarily represents the optimal t-PA agent under all circumstances. Therefore, several variants have been proposed or devised to enhance specific properties of t-PA. Certain of those variants address disadvantages associated with the use of natural t-PA in situations where an agent with a longer half-life or slower clearance rate would be preferred, e.g., in the treatment of deep-vein thrombosis and following reperfusion of an infarct victim, or where a single-chain agent is preferred.

For example, removal of a substantial portion or all of the finger domain results in a molecule with substantially diminished fibrin binding characteristics, albeit in return there is a decrease in the overall rate of clearance of the resultant entity. See WO 89/00197 published 12 Jan. 1989.

Variants are described in EPO Pat. Publ. No. 199,574 that have amino acid substitutions at the proteolytic cleavage sites at positions 275, 276, and 277. These variants, characterized preferentially as t-PA variants having an amino acid other than arginine at position 275, are referred to as protease-resistant one-chain t-PA variants in that, unlike natural t-PA, which can exist in either a one-chain or two-chain form, they are resistant to protease cleavage at position 275 and are therefore not converted metabolically in vivo into a two-chain form. This form is thought to have certain advantages biologically and commercially, in that it is more stable while the fibrin binding and fibrin stimulation are increased relative to two-chain t-PA. Furthermore, plasminogen activators are described that comprise one domain capable of interacting with fibrin and the protease domain of urokinase, with one embodiment being urokinase altered to make it less susceptible to forming two-chain urokinase. See WO 88/05081 published 14 Jul. 1988.

For further patent literature regarding modification of the protease cleavage site of t-PA, see, for example, EPO Pat. Nos. 241,209; EP 201,153 published Nov. 12, 1986; EP 233,013 published Aug. 19, 1987; EP 292,009 published Nov. 23, 1988; EP 293,936 published Dec. 7, 1988; and EP 293,934 published Dec. 7, 1988; and WO 88/10119.

Glycosylation mutants at 117-119, 184-186, and 448-450 exhibited higher specific activity as the mole percent carbohydrate was reduced. See EPO Pub. No. 227,462 published Jul. 1, 1987. This patent application additionally discloses using an assay of fibrin/fibrin degradation products and teaches that one may also modify the t-PA molecule at positions 272-280 or delete up to 25 amino acids from the C-terminus. Further, the t-PA mutants with Asn119, Ala186 and Asn450, which have the N-glycosylation sites selectively removed by DNA modification but contain residual O-linked carbohydrate, were found to be about two-fold as potent as melanoma t-PA in an in vitro lysis assay. See EPO Publ. No. 225,286 published Jun. 10, 1987.

Replacement of the amino acid at 449 of t-PA with any amino acid except arginine to modify the glycosylation site, as well as modification of Arg275 or deletion of the −3 to 91 region, is also taught. See WO 87/04722 published Aug. 13, 1987. An amino acid substitution at position 448 of t-PA is disclosed as desirable to remove glycosylation. See EPO Pub. No. 297,066 published Dec. 28, 1988. The combination of modifications at positions 448-450 and deletion of the N-terminal 1-82 amino acids is disclosed by WO 89/00191 published Jan. 12, 1989. Additionally, urokinase has been modified in the region of Asp302-Ser303-Thr304 to prevent glycosylation. See EPO Pub. No. 299,706 published 18 Jan. 1989.

However, alteration of the glycosylation sites, and in particular that at amino acid 117, seems invariably to result in a molecule having affected solubility characteristics that may result additionally in an altered circulating half-life pattern and/or fibrin binding characteristics. See EPO Pat. Publ. No. 238,304, published 23 Sep. 1987.

When the growth factor domain of t-PA is deleted, the resultant variant is still active and binds to fibrin, as reported by A. J. van Zonneveld et al., *Thrombos. Haemostas.*, 54 (1) 4 (1985). Various deletions in the growth factor domain have also been reported in the patent literature. See EPO Publ. No. 207,589 (substitutions and deletions between 51 and 87), EPO Publ. No. 241,209 (des-51-87), EPO Publ. No. 241,208 (des-51-87 and des-51-173), PCT 87/04722 (deletion of all or part of the N-terminal 1-91), EPO Publ. No. 231,624 (all of growth factor domain deleted), and EPO Publ. No. 242,836 and Jap. Pat. Appl. Kokai No. 62-269688 (some or all of the growth factor domain deleted).

It has further been shown that t-PA can be modified both in the region of the first kringle domain and in the growth factor domain, resulting in increased circulatory half-life. See EPO Pat. Publ. No. 241,208 published Oct. 14, 1987. The region between amino acids 51 and 87, inclusive, can be deleted from t-PA to result in a variant having slower clearance from plasma. Browne et al., *J. Biol. Chem.*, 263: 1599-1602 (1988). Also, t-pA can be modified, without adverse biological effects, in the region of amino acids 67 to 69 of the mature, native t-PA, by deletion of certain amino acid residues or replacement of one or more amino acids with different amino acids. See EPO Pat. Publ. No. 240,334 published Oct. 7, 1987. See also WO 89/12681 published Dec. 28, 1989 on substitutions at residues between 63-72, especially 66 and 67, of wild-type t-PA.

A hybrid of t-PA/urokinase using the region of t-PA encompassing amino acids 273-527 is also disclosed. See EPO 290,118 published Nov. 9, 1988.

Serpin-resistant mutants of human t-PA with alterations in the protease domain, including d296-302 t-PA, R304S t-PA, and R304E t-PA, are disclosed in Madison et al., *Nature*, 339: 721-724 (1989); see also the accompanying article by Dagmar Ringe in the same issue.

A general review of plasminogen activators and second-generation derivatives thereof can be found in Harris, *Protein Engineering*, 1: 449-458 (1987). Other reviews of t-PA variants include Pannekoek et al., *Fibrinolysis*, 2: 123-132 (1988) and Ross et al., in *Annual Reports in Medicinal Chemistry*, Vol. 23, Chapter 12 (1988).

It would be desirable to provide a t-PA molecule that, relative to wild-type t-PA, has a higher fibrin-stimulated (or a plasma clot-stimulated) activity than fibrinogen-stimulated (or plasma-stimulated) activity, i.e., is fibrin (or plasma clot) specific, so that it will act only at the site of the clot and not systemically.

Accordingly, it is an object of this invention to provide fibrin-specific t-PA molecules that exhibit improved therapeutic and pharmaceutical characteristics.

It is another object to provide for the treatment of conditions that admit the use of clot-dissolving agents that are active only at the site of the clot and are useful at higher levels than other such agents.

These and other objects will be apparent to one of ordinary skill in the art.

SUMMARY OF THE INVENTION

These objects are achieved by the provision of a human tissue plasminogen activator (t-PA) variant capable of exhibiting fibrin specificity or plasma clot specificity, characterized in that it comprises a deletion of the amino acids spanning positions 466 to 470 of the corresponding wild-type t-PA.

In further embodiments the invention provides DNA sequences and replicable vectors encoding the above-described variant and host cells transformed with them.

In yet another embodiment, the invention is directed to a composition for treating a vascular condition or disease comprising a therapeutically effective amount of the variant herein in admixture with a pharmaceutically acceptable carrier. Also encompassed herein is a composition for preventing fibrin deposition or adhesion formation or reformation comprising a therapeutically effective amount of the variant herein in admixture with a pharmaceutically acceptable carrier.

In still another embodiment, the invention provides a method of treating a vascular condition or disease in a mammal comprising administering an effective amount of the appropriate composition described above to the mammal.

The invention also provides a method of treating a mammal to prevent fibrin deposition or adhesion formation or reformation comprising administering to a site on the mammal of potential fibrin or adhesion formation an effective amount of the appropriate composition described above.

Practice of the invention results in a t-PA molecule that is more fibrin (or plasma clot) specific so that it will act more preferentially at the site of the clot than unmodified t-PA.

DETAILED DESCRIPTION OF THE PREFERRED EMBODIMENTS

A. Definitions

As used herein, the terms "human tissue plasminogen activator," "human t-PA," and "t-PA" denote human extrinsic (tissue-type) plasminogen activator having two functional regions consisting of a protease domain that is capable of converting plasminogen to plasmin and an N-terminal region believed to be responsible for fibrin binding. These three terms therefore include polypeptides containing these functional domains as part of the overall sequence. t-PA is suitably produced, e.g., by recombinant cell culture systems, in bioactive forms comprising the protease portion and portions of t-PA otherwise native to the source of the t-PA. It will be understood that natural allelic variations exist and occur from individual to individual, demonstrated by (an) amino acid difference(s) in the overall sequence.

As used herein, the term "wild-type t-PA" refers to the t-PA encoded by the cDNA reported by U.S. Pat. No. 4,766,075, supra, the disclosure of which is incorporated herein by reference. The t-PA thus encoded is suitably a t-PA molecule from any native source or any recombinant expression system, including 293 or 294 cells, Chinese hamster ovary cells, etc.

The expression "fibrin specificity" refers to the activity of a mutant that exhibits a higher ratio of fibrin-dependent specific activity to fibrinogen-dependent specific activity in a S-2251 assay (in either the one-chain or two-chain form) than wild-type rt-PA, and preferably a ratio of at least 1.5.

The expression "plasma clot specificity" refers to the activity of a mutant that exhibits a higher ratio of plasma clot-dependent specific activity to plasma-dependent specific activity in a S-2251 assay (in either the one-chain or two-chain form) than wild-type rt-PA, and preferably a ratio of at least 1.5.

As used herein, "transient expression system" denotes a cell culture containing cells transfected with a t-PA variant-encoding vector that expresses the DNA sequence encoding the variant transiently, i.e., in a manner that may not be stable. Such cells are deemed "capable of transient expression."

B. General Methods

1. Amino Acid Sequence Variants

Figure 1:
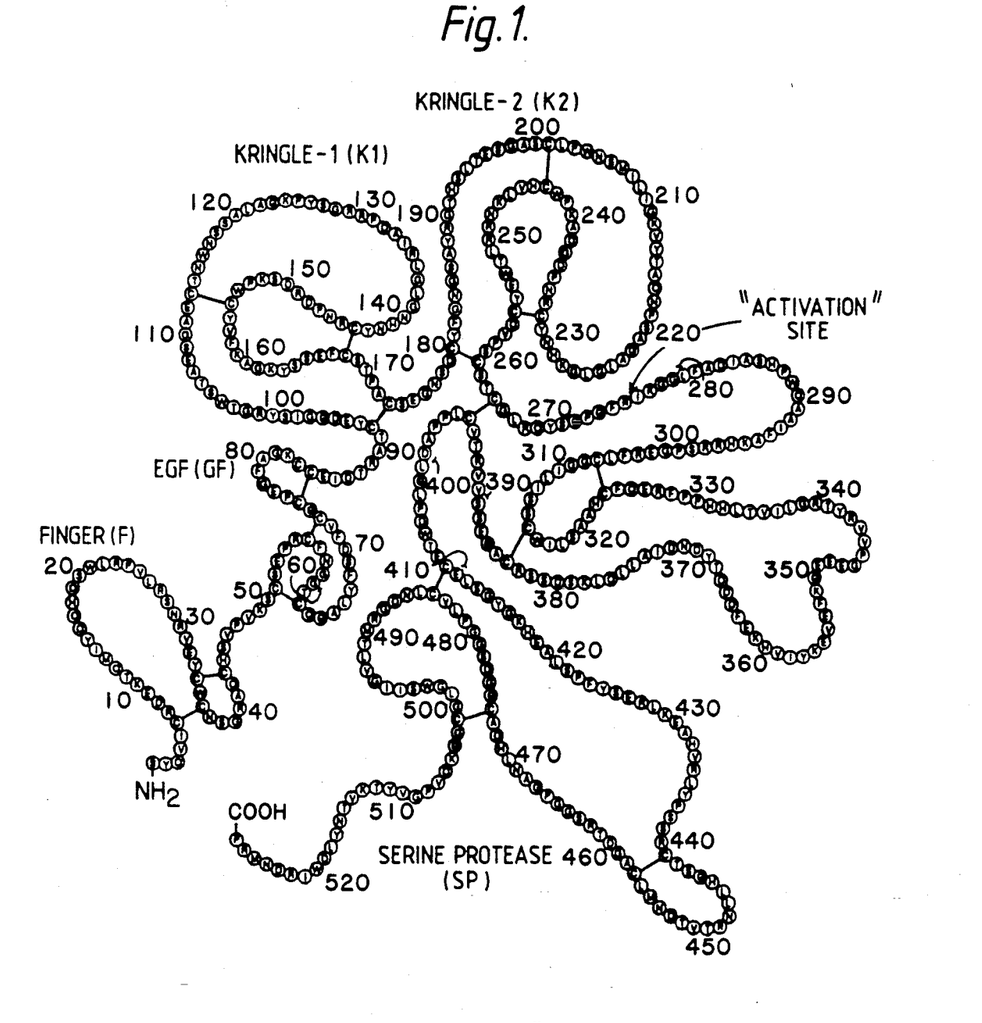
FIG. 1 depicts the primary structure of t-PA showing the location of the five domains, the disulfide bridging, and the activation site where the molecule is clipped into a two-chain molecule.

For purposes of discussing the variants herein, reference is made to FIG. 1, which illustrates the primary structure of t-PA.

In FIG. 1, the letters in the circles are single-letter amino acid codes, the connecting lines between chains indicate disulfide bridging, the open circles indicate glycosylation sites, and the designations F, GF, K1, K2, and SP indicate, respectively, the finger, growth factor, kringle 1, kringle 2, and serine protease domains.

For purposes of shorthand designation of t-PA variants described herein, it is noted that numbers refer to the amino acid residue/position along the amino acid sequences of putative mature t-PA (EPO Publ No. 93,619). Amino acid identification uses the single-letter alphabet of amino acids, i.e.,

| Asp | D | Aspartic acid |
|-----|---|---------------|
| Thr | T | Threonine |
| Ser | S | Serine |
| Glu | E | Glutamic acid |
| Pro | P | Proline |
| Gly | G | Glycine |
| Ala | A | Alanine |
| Cys | C | Cysteine |
| Val | V | Valine |
| Met | M | Methionine |
| Ile | I | Isoleucine |
| Leu | L | Leucine |
| Tyr | Y | Tyrosine |
| Phe | F | Phenylalanine |
| His | H | Histidine |
| Lys | K | Lysine |
| Arg | R | Arginine |
| Trp | W | Tryptophan |
| Gln | Q | Glutamine |
| Asn | N | Asparagine |

The designation for a deletion variant consists of the letter d followed by the number of the start position of the deletion to the number of the end position of the deletion, with the positions being based on the wild-type, mature t-PA. The designation for a substitution variant herein consists of a letter followed by a number followed by a letter. The first (leftmost) letter designates the amino acid in the wild-type, mature t-PA. The number refers to the amino acid position where the amino acid substitution is being made, and the second (right-hand) letter designates the amino acid that is used to replace the wild-type amino acid. The designation for an insertion variant consists of the letter i followed by a number designating the position of the residue in wild-type, mature t-PA before which the insertion starts, followed by one or more capital letters indicating, inclusively, the insertion to be made. Multiple mutations are separated by a comma in the notation for ease of reading them.

Examples of the nomenclature are as follows: the deletion variant herein where the amino acids at positions 466 to 470 are deleted from the wild-type, mature t-PA is designated d466-470. A substitution variant where the phenylalanine at position 305 of the wild-type t-PA is replaced with a histidine residue is designated F305H. A substitution variant with multiple substitutions at consecutive positions 296-299 of AAAA for KHRR is designated K296A,H297A,R298A,R299A. An insertion variant where cysteine and valine are inserted after position 305 of wild-type t-PA is designated i305CV. The notation 't-PA' follows after each mutant.

The t-PA variant herein, in addition to the deletion at positions 466-470, may also be altered from the native sequence at one or more other protease domain sites so as to display zymogenic and/or fibrin (or plasma clot) specific properties, as described in the parent applications to this application, copending namely, U.S. Ser. No. 07/384,608 filed Jul. 24, 1989, now U.S. Pat. No. 5,108,901 and U.S. Ser. No. 07/240,856 filed Sep. 2, 1988, now abandoned, the disclosures of which are incorporated herein by reference. Thus, the variant may contain zymogenic properties as well as being fibrin (or plasma clot) specific. The small regions of the protease domain that are altered may be identified as having charged amino acid side chains, which regions and/or regions adjacent thereto may be responsible for the interaction of t-PA with other substances that might affect its various activities.

The regions identified for testing for zymogenicity or fibrin-specific activity by the method described in Ser. No. 07/384,608 are at residue numbers 267, 283–287, 296–299, 303–304, 322, 326–327, 331–332, 339–342, 347–351, 353–356, 360–362, 364–366, 369–371, 378–383, 387–392, 400–405, 408, 410, 416–418, 426–430, 432–434, 440, 445–449, 449–453, 460–462, 471–472, 477, 487–489, 505–506, 513, 519–523, and 523–526 of the Corresponding wild-type t-PA.

One or more of these regions, or subunits thereof, may be altered, in addition to the deletion at positions 466–470, to determine if the desired biological property or properties will be obtained. The charged residues (Arg, Asp, His, Lys, and Glu) are suitably identified using a technique known as alanine-scanning mutagenesis, disclosed in Cunningham and Wells, *Science, 244:* 1081–1085 (1989), the disclosure of which is incorporated herein by reference, and replaced with a neutral or negatively charged amino acid to affect the interaction of the amino acids with the surrounding aqueous environment in or outside the cell.

Examples of such variants are those wherein amino acid substitutions are made at position(s) 267, 283+287, 296−299, 303−304, 331−332, 339+342, 347−349+351, 364−366, 408, 410, 416−418, 426−427+429−430, 432−434, 440, 445+449, 449+453, 460+462, and/or 477 of the corresponding wild-type t-PA, where the "+" indicates replacements only at the positions designated, and the "−" indicates replacements at all positions designated.

For the alanine scanning mutagenesis, it is preferable that an amino acid be substituted that will neutralize the charge of the corresponding amino acid of the wild-type t-PA, rather than confer an opposite charge on the molecule. Any hydrophobic, essentially uncharged or oppositely charged amino acid can be used, including, as preferred, alanine, glycine, serine, threonine, asparagine, glutamine, valine, leucine, isoleucine, phenylalanine, or tyrosine. Among these, small amino acids, such as alanine, serine and threonine, are preferred over larger amino acids such as valine, leucine, and isoleucine. Charged amino acids such as aspartic acid or glutamic acid are less preferred.

More preferably, the amino acid used for replacement is either alanine, serine, threonine, asparagine, glutamine, phenylalanine, or tyrosine, and more preferably still, alanine, serine, or threonine. Alanine is the most preferred amino acid for this purpose because it eliminates the side-chain beyond the beta-carbon and is less likely to alter the main-chain conformation of the wild-type t-PA molecule. Further, alanine is frequently found in both buried and exposed positions (Creighton, T. E., in *The Proteins* (eds. W. H. Freeman & Co., N.Y.); Chothia, C. (1976) *J. Mol. Biol.*, 150: 1).

The most preferred of these substitutions are an alanine residue in place of each of the existing residues at positions 296–299 of wild-type t-PA, i.e., K296A,H297A,R298A,R299A t-PA, at positions 416–418 of wild-type t-PA, i.e., K416A,H417A,E418A, at positions 426–427 and 429–430 of wild-type t-PA, i.e., E426A,R427A,K429A,E430A, at positions 339 and 342 of wild-type t-PA, i.e., R339A,R342A, and at positions 432 and 434 of wild-type t-PA, i.e., H432A,R434A. Thus, the preferred double-mutant t-PA molecules would be K296A,H297A,R298A,R299A,d466-470 t-PA, K416A,H417A,E418A,d466-470 t-PA, E426A,R427A,K429A,E430A,d466-470 t-PA, R339A,R342A,d466-470 t-PA, H432A,R434A,d466-470 t-PA, and combinations thereof, with E426A,R427A,K429A,E430A,d466-470 t-PA being particularly preferred.

Optional insertional variants that may exhibit zymogenic or fibrin-specific activity are those wherein one or more amino acids are inserted after the amino acids at positions 296, 297, 298, and/or 299. Preferred are those protease domain variants with an insertion consisting of either tyrosine, asparagine, lysine, arginine, or glutamine in addition to the deletion at positions 466–470.

Also, optionally the variant may contain substitutions, deletions, or insertions of residues in other regions of the native sequence to improve certain properties of the molecule, provided that changes are not made that prevent the cleavage of the one-chain form of t-PA to its two-chain form or otherwise alter the fibrin or plasma clot specificity conferred on the molecule by the deletions in the protease domain of the present invention. The preferred alterations in these other domains are provided below.

For example, the variants herein are suitably devoid of at least a portion of the finger domain, the growth factor domain, and/or the kringle 1 domain, and/or devoid of glycosylation potential at the glycosylation site surrounding amino acid 117 or 184, and suitably contain amino acid modifications in the putative lysine binding site of kringle 1 or 2.

In addition, fibrin binding of t-PA can be modulated, most preferably restored or increased, by appropriate substitutions of positively or negatively charged amino acid residues on the opposite edges of the putative ligand binding pocket of the kringle 2 domain of t-PA. The variants herein are generally prepared by site-directed mutagenesis or by excision/ligation techniques described further hereinbelow.

Specific examples of such variants include a molecule devoid of amino acids 1 to 44 (designated d1-44) and a molecule having aspartic acid at position 184 (designated N184D). Variants devoid of amino acids 1 to 44 are described more fully in WO 89/00197, supra.

All of the above variants are optionally modified in various other regions of the molecule, if such modifications still satisfy the criteria expressed herein for fibrin (or plasma clot) specific characteristics. Such modifications include, for example:

1. Kringle 1 modifications, for example, deletion of about 92 to 179, and/or
2. Kringle 2 modifications, for example, deletion of about 174–261 or modification in the region of amino acids about 205–215, especially 210–213, and/or
3. Amino acids about 244–255, especially 252 or its site, and/or
4. Amino acids about 233–242, especially 236–238, and/or
5. Known glycosylation sites such as amino acid 117 or 184, and/or
6. Addition of potential glycosylation sites as described in copending U.S. application Ser. No. 07/196,909 filed May 20, 1988, the disclosure of which is incorporated herein by reference. Briefly, a potential N- or O-linked glycosylation site is introduced into the t-PA molecule, for example, within its growth factor domain, preferably at position 67–69, where the tyrosine at position 67 is replaced with an asparagine residue, to alter the half-life of the t-PA molecule.

Many of these modifications may significantly alter clearance rates and fibrin binding relative to native t-PA. The practitioner skilled in the art will be able to determine by the appropriate assay what the optimum properties of each variant are that are desired in any particular instance.

The modification to delete, change, or insert the appropriate amino acid(s) in the native molecule to effect the above sequence variations is accomplished by any means known in the art, such as, e.g., site-directed mutagenesis or ligation of the appropriate sequence into the DNA encoding the relevant protein, as described below.

2. Site-Specific Mutagenesis

Preparation of t-PA variants in accordance herewith is preferably achieved by site-specific mutagenesis of DNA that encodes an earlier prepared variant or a nonvariant version of the protein. Site-specific mutagenesis allows the production of t-PA variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., *DNA*, 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.*, 153: 3 (1987)) may be employed to obtain single-stranded DNA.

In general, site-directed mutagenesis in accordance herewith is performed by first obtaining a single-stranded vector that includes within its sequence a DNA sequence that encodes the relevant t-PA. An oligonucleotide primer bearing the desired mutated sequence is prepared, generally synthetically, for example, by the method of Crea et al., *Proc. Natl. Acad. Sci. (USA)*, 75: 5765 (1978). This primer is then annealed with the single-stranded t-PA sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected, via hybridization to a radioactive probe consisting of the $^{32}$P-labeled mutagenesis primer, that include recombinant vectors bearing the mutated sequence arrangement.

After such a clone is selected, the mutated t-PA region may be removed and placed in an appropriate vector for t-PA production, generally an expression vector of the type that typically is employed for transformation of an appropriate eukaryotic host. In the context of the present invention, Chinese hamster ovary (CHO) cells or 293 (human kidney cells described by Graham et al., *J. Gen. Virol.*, 36: 59 (1977)) are preferred for the preparation of long-term stable t-PA producers. However, the invention is not limited to CHO production, as it is known that numerous other cell types are suitably employed, particularly where one desires only transient production of the enzyme for test purposes. For example, described below is a transient system employing 293 cells that provides a convenient system for production of t-PA variants for analytical purposes.

3. Cleavage/Ligation Technique

Another method for making mutations in the DNA sequence encoding the t-PA involves cleaving the DNA encoding the t-PA at the appropriate position by digestion with restriction enzymes, recovering the properly cleaved DNA, synthesizing an oligonucleotide encoding the desired amino acid and flanking regions such as polylinkers with blunt ends (or, instead of using polylinkers, digesting the synthetic oligonucleotide with the restriction enzymes also used to cleave the t-PA-encoding DNA, thereby creating cohesive termini), and ligating the synthetic DNA into the remainder of the t-PA-encoding structural gene.

4. Host Cell Cultures and Vectors

Although Chinese hamster ovary (CHO) expression ultimately is preferred for t-PA production, the vectors and methods disclosed herein are suitable for use in host cells over a wide range of eukaryotic organisms.

In general, of course, prokaryotes are preferred for the initial cloning of DNA sequences and constructing the vectors useful in the invention. For example, *E. coli* K12 strain 294 (ATCC No. 31,446) and *E. coli* strain W3110 (ATCC No. 27,325) are particularly useful. Other suitable microbial strains include *E. coli* strains such as *E. coli* B, and *E. coli* X1776 (ATCC No. 31,537). These examples are, of course, intended to be illustrative rather than limiting.

Prokaryotes also are useful for expression. The aforementioned strains, as well as bacilli such as *Bacillus subtilis*, and other enterobacteriaceae such as, e.g., *Salmonella typhimurium* or *Serratia marcesans*, and various Pseudomonas species are examples of useful hosts for expression.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang et al., *Nature*, 375: 615 (1978); Itakura et al., *Science*, 198: 1056 (1977); Goeddel et al., *Nature*, 281: 544 (1979)) and a tryptophan (trp) promoter system (Goeddel et al., *Nucl. Acids Res.*, 8: 4057 (1980); EPO Appl. Publ. No. 36,776), and the alkaline phosphatase systems. While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell*, 20: 269 (1980)).

In addition to prokaryotes, eukaryotic microbes, such as yeasts, also are suitably used herein. *Saccharomyces cerevisiae*, or common baker's yeast, is the most commonly used among eukaryotic microorganisms, although a number of other strains are commonly available. For example, for expression in Saccharomyces, the plasmid YRp7 (Stinchcomb et al., *Nature*, 282: 39 (1979); Kingsman et al., *Gene*, 7: 141 (1979); Tschemper et al., *Gene*, 10: 157 (1980)) is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland et al., *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, CHO cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., *Nature*, 273: 113 (1978)). Smaller or larger SV40 fragments are also suitably used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication typically is provided either by construction of the vector to include an exogenous origin, such as may be derived from SV40 or other viral (e.g., Polyoma, Adeno, VSV, BPV) source, or by the host cell chromosomal replication mechanism. If the vector is integrated into the host cell chromosome, the latter is often sufficient.

Satisfactory amounts of human t-PA are produced by cell cultures; however, refinements, using a secondary coding sequence, serve to enhance production levels even further. The secondary coding sequence comprises dihydrofolate reductase (DHFR) that is affected by an externally controlled parameter, such as methotrexate (MTX), thus permitting control of expression by control of the MTX concentration.

In the selection of a preferred host cell for transfection by the vectors of the invention that comprise DNA sequences encoding both variant t-PA and DHFR protein, it is appropriate to consider the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated, as described by Urlaub and Chasin, *Proc. Natl. Acad. Sci*, (USA) 77: 4216 (1980).

On the other hand, if DHFR protein with low binding affinity for MTX is used as the controlling sequence, it is not necessary to use DHFR-deficient cells. Because the mutant DHFR is resistant to MTX, MTX-containing media can be used as a means of selection, provided that the host cells are themselves MTX sensitive. Most eukaryotic cells that are capable of absorbing MTX appear to be sensitive to MTX. One such useful cell line is a CHO line, CHO-K1 (ATCC No. CCL 61).

5. Typical Cloning and Expression Methodology Employable

If mammalian cells are used as host cells, transfection generally is carried out by the calcium phosphate precipitation method as described by Graham and Van der Eb, *Virology*, 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.*, 75: 1929-1933 (1978).

If prokaryotic cells or cells that contain substantial cell wall constructions are used, the preferred method of transfection is calcium treatment using calcium as described by Cohen et al., *Proc. Natl. Acad. Sci.* (USA) 69: 2110 (1972), or more recently electroporation.

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of the Klenow fragment of DNA Polymerase I (Klenow), phenol-chloroform extracted, and ethanol precipitated.

Size separation of the cleaved fragments is performed using 6 percent polyacrylamide gel described by Goeddel et al., *Nucleic Acids Res.*, 8: 4057 (1980).

For ligation, approximately equimolar amounts of the desired components, suitably end tailored to provide correct matching, are treated with about 10 units T4 DNA ligase per 0.5 μg DNA. (When cleaved vectors are used as components, it may be useful to prevent a religation of the cleaved vector by pretreatment with bacterial alkaline phosphatase.)

As discussed above, t-PA variants are preferably produced by means of specific mutation. Variants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation being traversed.

For analysis to confirm correct sequences in plasmids constructed, the ligation mixtures are typically used to transform *E. coli* K12 strain 294 (ATCC No. 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9: 309 (1981) or by the method of Maxam et al., *Methods of Enzymology*, 65: 499 (1980), 5 After introduction of the DNA into the mammalian cell host and selection in medium for stable transformants, amplification of DHFR-protein-coding sequences is effected by growing host cell cultures in the presence of approximately 200-500 nM concentrations of MTX, a competitive inhibitor of DHFR activity. The effective range of concentration is highly dependent, of course, upon the nature of the DHFR gene and protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In order to simplify the examples certain frequently occurring methods will be referenced by shorthand phrases.

"Plasmids" are designated by a low case p followed by an alphanumeric designation. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., *Molecular Cloning: A Laboratory Manual* (Cold Spring Harbor Labortory Press, New York, 1982), pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, *Nucleic Acids Res.* 9:6103-6114, and D. Goeddel et al., 1980, *Nucleic Acids Res.* 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, *J. Mol. Biol.* 98: 503-517, and hybridization as described by T. Maniatis et al., 1978, *Cell* 15: 687-701.

"Transformation" means introducing DNA into an organism so that the DNA is replicable, either as an extrachromosomal element or chromosomal integrant. Unless otherwise provided, the method used herein for transformation of *E. coli* is the CaCl$_2$ method of Mandel et al., 1970, *J. Mol. Biol.* 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id., p. 90, may be used.

"Oligonucleotides" are short length single or double stranded polydeoxynucleotides that are chemically synthesized by known methods and then purified on polyacrylamide gels.

C. Purification

The t-PA variant preferably is recovered from the culture medium as a secreted protein, although it also may be recovered from host cell lysates when directly expressed without a secretory signal. When the variant is expressed in a recombinant cell other than one of human origin, the variant is thus completely free of proteins of human origin. However, it is necessary to purify the variant from recombinant cell proteins in order to obtain preparations that are substantially homogeneous as to protein. As a first step, the culture medium or lysate is centrifuged to remove particulate cell debris.

The variant is then purified from contaminant soluble proteins, for example, by fractionation on immunoaffinity or ion exchange columns; ethanol precipitation; reverse phase HPLC; chromatography on silica or on a cation exchange resin such as DEAE; chromatofocusing; SDS-PAGE; ammonium sulfate precipitation; or gel electrophoresis using, for example, Sephadex G-75. A protease inhibitor that does not interfere with the t-PA activity such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native t-PA may require modification to account for changes in the character of t-PA or its variants upon expression in recombinant cell culture.

In a preferred embodiment, the t-PA variant is secreted, and the supernatant is passed over a PBS-preconditioned column of glass beads coupled to anti-t-PA goat polyclonal A6 antibody, the column is equilibrated with a buffer, and the t-PA variant is then eluted.

D. Pharmaceutical Compositions

The compounds of the present invention can be formulated according to known methods to prepare pharmaceutically useful compositions, whereby the t-PA product hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences*, 16th ed., 1980, Mack Publishing Co., edited by Oslo et al., the disclosure of which is hereby incorporated by reference. Such compositions will typically contain an effective amount of the variant herein, for example, from about 0.5 to about 5 mg/ml, together with a suitable amount of carrier vehicle to prepare pharmaceutically acceptable compositions suitable for effective administration to the host. The t-PA variant herein may be administered parenterally to subjects suffering from cardiovascular diseases or conditions, or by other methods that ensure its delivery to the bloodstream in an effective form.

Compositions particularly well suited for the clinical administration of variant t-PA products employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned For example, in the treatment of deep vein thrombosis or peripheral vascular disease, "bolus" doses, on the order of about 0.05 to about 0.2 mg/kg, will typically be preferred with subsequent administrations, on the order of about 0.1 to about 0.2 mg/kg, being given to maintain an approximately constant blood level, preferably on the order of about 3 μg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus on the order of about 0.3 mg/kg.

For example, the t-PA variant hereof is suitably administered parenterally to subjects suffering from cardiovascular diseases or conditions. Dosage and dose rate may be parallel to or higher than that currently in use in clinical investigations of other cardiovascular, thrombolytic agents, e.g, about 1-2 mg/kg body weight as an intravenous or intra-arterial dose over 1.5 to 12 hours in human patients suffering from myocardial infarction, pulmonary embolism, etc. Higher doses may be tolerated because the variants herein have lower side effects than wild-type t-PA, leading to faster and more complete clot lysis.

As one example of an appropriate dosage form, a vial containing 50 mg t-PA, arginine, phosphoric acid, and polysorbate 80 is reconstituted with 50 ml sterile water for injection and mixed with a suitable volume of 0.9 percent sodium chloride injection.

The t-PA variant herein also is useful to prevent fibrin deposition or adhesion formation or reformation. One embodiment of this use is described in copending U.S. Ser. No. 07/125,319 filed Nov. 25, 1987, the disclosure of which is incorporated herein by reference. Generally, such treatment involves topical administration of a composition to a site of potential fibrin or adhesion formation wherein the composition comprises a therapeutically effective amount of the t-PA variant in a sparingly soluble form that is continuously released at that site for a period of time of about from three days to two weeks. Typically, the t-PA variant is administered at a dosage sufficient to prevent fibrin deposition or formation of adhesions following surgery, infection, trauma, or inflammation. Typically, this amount is from 0.02 mg/g of gel to 25 mg/g of gel, with preferred amounts from 0.20 mg/g gel to about 2.5 mg/g of gel, most preferably from 0.25 mg/g to about 1.0 mg/g of gel.

The vehicle in which the t-PA is typically formulated for preventing adhesion formation in a semisolid, mucilaginous pharmaceutically inert carrier for positioning the enzyme at the site of potential adhesion formation. Such a carrier includes long-chain hydrocarbons or vegetable oils and waxes composed of mixtures of saturated and unsaturated fatty acid glycerides or mixtures of modified saturated and unsaturated fatty acid glycerides. Examples include semisolid vehicles such as petroleum jelly or semi-synthetic glycerides, polyhydroxy solvents such as glycerol, long-chain hydrocarbons, bioerodable polymers, or liposomes.

The following examples are intended merely to illustrate the best mode now known for practicing the invention, but the invention is not to be considered limited thereto.

All literature and patent application citations herein are expressly incorporated by reference.

EXAMPLE I

1. Construction of pRK7-t-PA

Plasmid pRK7 was used as the vector for generation of the t-PA mutant. pRK7 is identical to pRK5 (EP Pub. No. 307,247 published Mar. 15, 1989), except that the order of the endonuclease restriction sites in the polylinker region between ClaI and HindIII is reversed. The t-PA cDNA (Pennica et al., *Nature*, 301: 214 (1983)) was prepared for insertion into the vector by cutting with restriction endonuclease HindIII (which cuts 49 base pairs 5' of the ATG start codon) and restriction endonuclease BalI (which cuts 276 base pairs downstream of the TGA stop codon). This cDNA was ligated into pRK7 previously cut with HindIII and SmaI using standard ligation methodology (Sambrook et al., *Molecular Cloning: A Laboratory Manual*, 2nd ed. (Cold Spring Harbor Laboratory Press, New York, 1989)). This construct was named pRK7-t-PA.

2. Site-Directed Mutagenesis of pRK7-t-PA

Site-directed mutagenesis of t-PA cDNA was performed by the method of Taylor et al., *Nucl. Acids. Res.*, 13: 8765 (1985) using a kit purchased from the Amersham Corporation (catalog number RPN 1253). For generation of the desired mutant, an oligonucleotide having a sequence coding for the desired amino acid deletion was synthesized and used as a primer. This oligonucleotide was annealed to single-stranded pRK7-t-PA that had been prepared by standard procedures (Viera et al., *Meth. Enz.*, 143: 3 (1987)).

A mixture of three deoxyribonucleotides, deoxyriboadenosine (dATP), deoxyriboguanosine (dGTP), and deoxyribothymidine (dTTP), was combined with a modified thio-deoxyribocytosine called dCTP(aS) provided in the kit by the manufacturer of the kit, and added to the single-stranded pRK7-t-PA to which was annealed the oligonucleotide.

Upon addition of DNA polymerase to this mixture, a strand of DNA identical to pRK7-t-PA except for the deleted bases was generated. In addition, this new strand of DNA contained dCTP(aS) instead of dCTP, which served to protect it from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule that was only partly single-stranded. A complete double-stranded DNA homoduplex molecule was then formed by DNA polymerase in the presence of all four deoxyribonucleotide triphosphates, ATP, and DNA ligase.

The following oligonucleotide was prepared to use as a primer to generate the pRK7-t-PA molecule with the desired deletion of P466, Q467, A468, N469, and L470:

5'-CTGGCAGGCGTCGTGCCCGCCGCTC-CGAGT-3'

3. Bacterial Transformation and DNA Preparation

The mutant t-PA construct generated using the protocol above was transformed into *E. coli* host strain MM294tonA using the standard CaCl$_2$ procedure (Sambrook et al., supra) for preparation and transformation of competent cells. MM294tonA (which is resistant to T1 phage) was prepared by the insertion and subsequent imprecise excision of a Tn10 transposon into the tonA gene. This gene was then inserted, using transposon insertion mutagenesis (Kleckner et al., *J. Mol. Biol.*, 116: 125-159 (1977)), into *E. coli* host MM294 (ATCC No. 31,446).

DNA was extracted from individual colonies of bacterial transformants using the standard miniprep procedure of Sambrook et al., supra. The plasmids were further purified by passage over a Sephacryl CL6B spin column, and then analyzed by sequencing and by restriction endonuclease digestion and agarose gel electrophoresis.

4. Transfection of Human Embryonic Kidney 293 Cells (Small-Scale)

293 cells were grown to 70% confluence in 6-well plates. 2.5 μg of t-PA plasmid DNA mutant was dissolved in 150 μl of 1 mM Tris-HCl, 0.1 mM EDTA, 0.227M CaCl$_2$. Added to this (dropwise while vortexing) was 150 μl of 50 mM HEPES buffer (pH 7.35), 280 mM NaCl, 1.5 mM NaPO$_4$, and the precipitate was allowed to form for ten min. at 25° C. The suspended precipitate was then added to the cells in the individual wells in a 6-well plate and allowed to settle for four hours in the incubator. The medium was then aspirated off and 1 ml of 20% glycerol in PBS was added for 30 sec. The cells were washed twice, first with 3 ml, then with 1 ml, of serum-free medium. Then 3 ml of fresh medium was added and the cells were incubated for five days. The medium was then collected and assayed.

When single-chain t-PA was required, the procedure was as described above except that plasminogen-depleted serum was used during the growth phase of the cells.

5. Biological Assays

A. t-PA Quantitation

The amount of t-PA present in the cell culture supernatant was determined by the ELISA procedure using polyclonal antibodies prepared against wild-type t-PA. The t-PA was found to be homogeneous.

B. S-2288 Assay

The S-2288 assay was used to measure the proteolytic activity of the mutant in both the one- and two-chain forms. This assay is a direct assay for t-PA proteolytic activity; t-PA cleaves the bond between the small peptide and the paranitroanilide chromophore of the S-2288 substrate.

Standard curve samples were prepared by diluting wild-type rt-PA with cell culture media. The standard curve samples and rt-PA mutant sample were added to the wells of a microtiter plate. If the assay was used to measure the activity of two-chain rt-PA, an incubation step with human plasmin was included in the procedure. Human plasmin (KabiVitrum) was added to a final concentration of 0.13 CU (casein units)/ml. The samples were incubated for 90 minutes at room temperature. For assaying the samples in the single-chain form, the plasmin solution was replaced by PBS and the 90-minute incubation was omitted.

Aprotinin [Sigma, approximately 14 TIU (trypsin inhibitor unit)/mg] was added to a final concentration of 72 $\mu$g/ml to inhibit the plasmin activity, and the samples were incubated at room temperature for 15 minutes. A 2.16 mM solution of S-2288 (KabiVitrum) was diluted to 1.45 mM with 0.1M Tris, 0.106 mM NaCl, 0.02% sodium azide, pH 8.4, and 100 $\mu$l of this solution was added to each well of the microtiter plate (final volume in each well was 200 $\mu$l). Color development was monitored at 405 nm. The slope of the absorbance vs. time curve for each standard and the sample was determined. A standard curve was prepared by plotting the slope of the absorbance vs. time curve as a function of rt-PA concentration for the rt-PA standards. The relative activity concentration of the mutant was then determined from the standard curve. The activity concentration of the mutant was divided by the concentration for the mutant obtained in the rt-PA ELISA, and the resulting specific activity was expressed relative to wild-type t-PA, which was assigned a value of 1.0.

C. S-2251 Assay

This assay is an indirect assay for t-PA activity. In this assay, plasminogen is converted to plasmin by the action of t-PA, and plasmin cleaves the S-2251 substrate to release the paranitroanilide chromophore. Production of this chromophore is then measured over time.

1. Fibrin-Stimulated S-2251 Assay

Standard curve samples were prepared as described for the S-2288 assay. For assay in the two-chain form, the sample was incubated with plasmin-Sepharose. Plasmin-Sepharose was prepared by coupling approximately 20.8 CU of human plasmin (KabiVitrum) to 1 ml of cyanogen bromide activated Sepharose (Pharmacia). The plasmin-Sepharose (50 $\mu$l of a 5% slurry) was incubated with shaking for 90 min. at room temperature with 150 $\mu$l of sample. Following the incubation, the resin was removed by centrifugation, and 10 $\mu$l of sample was added to the wells of a microtiter plate.

For assay in the one-chain form, 50 $\mu$l of cell culture media was added in place of resin, and the incubation step was omitted. Human thrombin (10 $\mu$l of a 42 unit/ml solution) was added to the well. The reaction in the well was started by the addition of a cocktail (130 $\mu$l) composed of 28 $\mu$l of human Glu-plasminogen (5.3 $\mu$M); 10 $\mu$l of plasminogen-free human fibrinogen (10 $\mu$M); 30 $\mu$l of 3 mM S-2251 (KabiVitrum); and 62 $\mu$l of PBS. Color development was monitored at 405 nm, and the absorbance at the reference wavelength of 492 nm was subtracted from each time point. The slope of the absorbance vs. time squared curve was determined for the standard and mutant samples. A standard curve was prepared by plotting the slope of the absorbance vs. time squared curve as a function of rt-PA concentration for the rt-PA standards. The determination of the relative specific activity for the mutant was as described for the S-2288 assay.

2. Fibrinogen-Stimulated S-2251 Assay

This assay was performed as described for the fibrin-stimulated S-2251 assay except that PBS was substituted for the thrombin.

3. Plasma Clot S-2251 Assay

The standard curve sample preparation and the conversion of one-chain rt-PA to two-chain rt-PA using plasmin-Sepharose were as described for the fibrin-stimulated S-2251 assay. Human thrombin (10 $\mu$l of a 31 $\mu$g/ml solution) was added to each well of the microtiter plate. The standard and mutant samples (40 $\mu$l) were added to the plate and the reaction was started by adding 100 $\mu$l of a mixture of 90 $\mu$l of acid citrate dextrose human plasma and 10 $\mu$l of 9.1 mM S-2251 (KabiVitrum). Color development was monitored at 405 nm and the absorbance at the reference wavelength of 492 nm was subtracted from each time point. The analysis of the data was as described for the fibrin-stimulated S-2251 assay.

4. Plasma S-2251 Assay

This assay was performed as described for the plasma clot S-2251 assay except that PBS was substituted for the thrombin.

6. Results

The deletion mutant was assayed for zymogenic qualities and fibrin specificity using the fibrin-dependent and plasma clot-dependent assays. The results are shown in Table I. Values are averages of two determinations, except for the one-chain S-2251 fibrin-stimulated and plasma-clot-stimulated assays, which are a single determination.

TABLE I

| Assay | Relative Activity to Wild-Type t-PA |
|---|---|
| Direct chromogenic assay (S-2288) (2-chain) | 0.55 |
| Direct chromogenic assay (S-2288) (1-chain) | 0.33 |
| Plasminogen activator assay (S-2251) unstimulated (2-chain) | 0.34 |
| Plasminogen activator assay (S-2251) fibrinogen stimulated (2-chain) | 0.11 |
| Plasminogen activator assay (S-2251) fibrin stimulated (2-chain) | 1.13 |
| Plasminogen activator assay (S-2251) | 1.05 |

TABLE I-continued

| Assay | Relative Activity to Wild-Type t-PA |
|---|---|
| fibrin stimulated (1-chain) Plasminogen activator assay (S-2251) in plasma (2-chain) | 0.11 |
| Plasminogen activator assay (S-2251) in a plasma clot (2-chain) | 1.03 |
| Plasminogen activator assay (S-2251) in a plasma clot (1-chain) | 0.92 |
| Plasminogen activator assay (S-2251) fibrin/fibrinogen stimulation (2-chain) | 10.06 |
| Plasminogen activator assay (S-2251) plasma clot/plasma (2-chain) | 9.10 | d

The results show that the d466-470 t-PA variant is approximately 10-fold more fibrin specific and 9-fold more plasma clot specific in plasminogen activation than wild-type t-PA. The molecule is not zymogenic.

What is claimed is:

1. A human tissue plasminogen activator (t-PA) variant having fibrin specificity or plasma clot specificity, wherein said t-PA variant comprises d466-470 t-PA.

2. The variant of claim 1 having an amino acid substituted within positions 269-299, inclusive, of wild-type human t-PA.

3. The variant of claim 2 having at least two amino acids substituted within positions 296-299, inclusive, of wild-type human t-PA.

4. The variant of claim 3 wherein the substitution is with alanine residues.

5. The variant of claim 1 that is devoid of amino acids 1 to 44 of wild-type human t-PA.

6. The variant of claim 1 that has at least one amino acid selected from the group of amino acid positions 117-119 and 184-186 substituted with another amino acid such that glycosylation does not occur at amino acid 184 or 117 of wild-type human t-PA.

7. The variant of claim 1 that contains an asparagine substituted at position 67 of the corresponding wild-type t-PA.

8. The variant of claim 1 that is devoid of amino acids 92-179, inclusive, of wild-type human t-PA.

9. A composition for treating a vascular condition or disease comprising a therapeutically effective amount of the variant of claim 1 in admixture with a pharmaceutically acceptable carrier.

10. A method of treating a vascular condition or disease in a mammal comprising administering an effective amount of the composition of claim 9 to the mammal.

* * * * *